United States Patent [19]

Walsdorf et al.

[11] Patent Number: 4,814,177

[45] Date of Patent: Mar. 21, 1989

[54] ULTRADENSE AND MORE SOLUBLE AND BIOAVAILABLE PREPARATIONS OF CALCIUM CITRATE

[75] Inventors: Neill B. Walsdorf; George Alexandrides, both of San Antonio; Charles Y. C. Pak, Dallas, all of Tex.

[73] Assignees: Board of Regents, University of Texas System, Austin; Mission Pharmacal, San Antonio, both of Tex.

[21] Appl. No.: 896,651

[22] Filed: Aug. 13, 1986

Related U.S. Application Data

[63] Continuation-in-part of Ser. No. 840,884, Mar. 18, 1986, abandoned.

[51] Int. Cl.$^4$ .................. A61K 9/20; A61K 33/00; A61K 33/06
[52] U.S. Cl. .................. 424/464; 424/127; 424/154; 514/891
[58] Field of Search .................. 424/464, 127, 154; 427/3; 514/891

[56] References Cited

U.S. PATENT DOCUMENTS

| | | | |
|---|---|---|---|
| 3,105,792 | 10/1963 | White | 167/57 |
| 3,653,914 | 4/1972 | Schmitt | 264/122 X |
| 4,107,346 | 8/1978 | Kravitz | 426/648 |
| 4,185,093 | 1/1980 | Carnes et al. | 424/153 |
| 4,214,996 | 7/1980 | Buddemeyer et al. | 252/1 |
| 4,289,750 | 9/1981 | Kopp et al. | 424/33 |
| 4,405,596 | 9/1983 | Helbig et al. | 424/33 |
| 4,551,342 | 11/1985 | Nakel et al. | 426/548 |
| 4,614,648 | 9/1986 | Bru | 424/44 |
| 4,772,467 | 9/1988 | Pak | 424/127 |

FOREIGN PATENT DOCUMENTS

| | | |
|---|---|---|
| 0075429 | 3/1983 | European Pat. Off. |
| 761525 | 7/1944 | Fed. Rep. of Germany |
| 3014503 | 10/1981 | Fed. Rep. of Germany |
| 4384M | 8/1966 | France |
| 7100516 | 6/1969 | Japan |
| WO/05552 | 12/1985 | PCT Int'l Appl. |
| 193065 | 1/1938 | Switzerland |
| 597936 | 2/1948 | United Kingdom |

OTHER PUBLICATIONS

Packett et al., date unavailable, "Mineral Studies in Ovine Phosphatic Urolithiasis", pp. 1716–1720.
Skillman (Consultant, Feb. (1984)).
Hunt and Johnson (Digestive Dis. and Sci., 28:417 (1983)).
Unlisted Drugs (1976), reference C.
Rote Liste (1961).
Pogainis and Shaw (Proc. S. D. Acad. Sci., XXXVI, p. 56 (1957)).
Chatterjee and Dhar (J. Phys. Chem., 28:1009 (1924)).
Sep. 11, 1986 News Release from Proctor and Gamble.
Bonnick (Letter to Newsweek, Feb. 17, 1986).
Kolata (Science, 233:519, (1986)).
Bishop Article from the Wall Street Journal (1986).
Abstract by Riggs et al. (1986).
Abstract by Christiansen et al. (J. Bone Min. Res., 1 (1986)).
Abstract by Markovic et al. (1986).
Brody (NY. Times, Dec. 17, 1985).
Pekkanen (Reader's Digest, Nov. 1985).
Rubin Newspaper Clipping (Austin American Statesman, Nov. 15, 1985).
Edelstein (1985) Article from Ladies Home Journal.
Harvey et al. (J. Clin. Endocrin. Met., 61:1223 (1985)).
Nicar and Pak (J. Clin. Endocrin, Met.), 61:391 (1985)).
Sakhaee et al. (J. Clin. Endocrine, Met., 61:368 (1985)).
Bo-Linn et al. (J. Clin. Invest., 73:640 (1984)).
Consensus Development Conference Statement from the National Institute of Health (1984).
Kurtz et al. (Science, 222:1139 (1984)).
Ackley et al. (Am. J. Clin. Nutr., 38:457 (1983)).
Belizan (J. Am. Med. Ass'n., 249:1161 (1983 #1).
Belizan et al. (Am. J. Obstet. Gynecol., 146:175 (1983 #2)).
Nordenvall et al. (Eur. Urol., 9:35 (1983)).
McCarron et al. (Science, 217:267 (1982)).
Riggs et al. (New Eng. J. Med., 306:446 (1982)).
Strauss et al. (Am. J. Med., 72:17 (1982)).
Leskovar et al. (Urol. Int., 36:325 (1981)).
Butz and Rost (5th Symp. on Exptl. Urol., p. 243 (1980)).

(List continued on next page.)

Primary Examiner—Michael Lusignan
Attorney, Agent, or Firm—Arnold, White & Durkee

[57] ABSTRACT

A calcium citrate composition having a bulk density greater than about 1.1 g/cc. Citric acid and a calcium compound are mixed to produce a mixture having a calcium compound/citric acid molar ratio of about 1.5. A hydrated mixture percent is produced by agitatively adding water to the mixture, although when desired the calcium compound, citric acid and water may be mixed in one step. The hydrated mixture is blended to facilitate the reaction of citric acid with the calcium compound and to form a granulated mass primarily consisting of granules with diameters between about 1/64 inch and about 1/16 inch. The granulated mass is then dried to a moisture content of between about 10 weight percent and about 13 weight percent to produce a calcium citrate composition having a bulk density greater than about 1.1 g/cc.

For calcium citrate tablets this calcium citrate composition is formed into a tableting composition by subjoining one or more tableting binders. The tableting composition is then fed through a multiple-station tablet press to form high density calcium citrate tablets.

The high density calcium citrate tablets are greater than about 15 weight percent calcium and have a calcium/citrate molar ratio of about 1.5. Such tablets characteristically have a density greater than about 1.5 g/cc and may, for aesthetic or other purposes, be coated with mixtures comprising substances such as sugar, polyvinylpyrrolidone, calcium carbonate and titanium dioxide.

44 Claims, No Drawings

OTHER PUBLICATIONS

Hartung et al. (idem (1980)).
Nordin et al. (Brit. Med. J., Feb. 16, 1980, p. 451).
Rudman et al. (N. Eng. J. Med., 303:657 (1980)).
Barilla et al. (Am. J. Med., 64:579 (1978)).
Heaney et al. (J. Lab. Clin. Med. 92:953 (1978)).
Pak (Calcium Nephrolithiasis, Plenum, N.Y., p. 5 (1978)).
Recker et al. (Ann. Int. Med., 87:649 (1977)).
Pak (Urolithiasis Res., Plenum, N.Y., p. 213 (1976)).
Pak et al. (J. Clin. Invest., 54:387 (1974 #1).
Pak et al. (N. Eng. J. Med., 290:175 (1974 #2)).
Peacock et al., (Brit. Med. J., Jun., p. 729 (1968)).
Clarkson et al. (Clin. Sci., 30:425 (1966)).
McDonald et al. (Clin. Sci., 26:27 (1964)).
Dialog Search of the Patent and Scientific Literature.
Packett, et al. (1968) *J. Animal Science* 27:1716–1721.

ULTRADENSE AND MORE SOLUBLE AND BIOAVAILABLE PREPARATIONS OF CALCIUM CITRATE

BACKGROUND OF THE INVENTION

A portion of the development of the present invention was supported by Grant No. P01-AM 20543 from the United States Government, National Institutes of Health.

This is a continuation-in-part of co-pending U.S. patent application Ser. No. 840,884, filed Mar. 18, 1986, now abandoned.

The mineral calcium is an important human dietary component. Calcium is required for adequate bone formation and maintenance, as well as for diverse metabolic functions. These diverse metabolic functions of calcium are incompletely understood but likely to involve, at least in part, the alteration and functional control of proteins such as enzymes.

An assurance of adequate dietary calcium intake is thus important for normal development, metabolism and maintenance. Dietary calcium intake alone however is insufficient to assure that adequate calcium levels are available for required body functions. Dietary calcium must be absorbed from the digestive tract before it may be utilized. Furthermore, the urinary excretion of absorbed calcium must be considered, particularly for individuals who may be subject to the formation of calcium-containing kidney stones.

The intestinal absorption of calcium is enhanced by vitamin D and may also be affected by the particular chemical form of ingested calcium.

Among the conditions of particular relevance to calcium dietary requirements is osteoporosis. Osteoporosis, a condition characterized by decreases in bone mass, renders bones more fragile and susceptible to fracture. The increasingly older population of this country, since osteoporosis is usually an age-related phenomenon, further accentuates the significance of this condition. Post-menopausal women are generally agreed to be most susceptible to osteoporosis. As demonstrated by Heaney et al (J. Lab. Clin. Med. (1978) Vol. 92 No. 6 pp. 953 to 963), postmenopausal women, unless treated with estrogens, required an increased calcium-intake to maintain a zero calcium balance. This increased required intake was ascribed as due to a decrease in the production of an active vitamin D compound and decrease in calcium absorption, both perhaps related to the absence of estrogens. Recker et al (Annal Int. Med. (1977) Vol. 87 No. 6 pp. 649 to 655) demonstrated that further bone losses in osteoporosis prone postmenopausal women may be prevented by estrogen treatment or, to a lesser extent, by dietary calcium supplementation with calcium carbonate.

In an additional study concerning osteoporosis of postmenopausal women, Nordin et al (Brit. Med. J. (1980) Vol. 280 pp. 451 to 454) found three treatments that succeeded in lessening or abolishing further bone deterioration. These three treatments were: dietary calcium supplementation; estrogenic hormone treatment; and, treatment with estrogenic hormone plus 1 alpha hydroxy vitamin $D_3$.

Treatment of individuals with estrogenic hormones may have adverse effects, such as the stimulation of estrogen-dependent tumors. Treatment of individuals with vitamin D derivatives may be inadvisable because of potentially toxic effects when excess vitamin D is administered. An effective dietary calcium supplementation appears to be an advisable treatment for osteoporosis.

In certain individuals however, dietary calcium supplementation may increase urinary calcium and lead to formation of calcium-containing kidney stones (nephrolithiasis).

Kidney stone formation may result from a number of conditions, one of which is the presence of undue amounts of calcium in urine. Pak et al (N. Eng. J. Med. (1974) Vol. 290 pp. 175 to 180) have shown that urinary calcium levels and renal calcium stone formation are decreased when patients with a history of recurrent calcium nephrolithiasis are fed low calcium diets and treated orally with cellulose phosphate. Pak (Urolithiasis Research (1976) ed. by H. Fleisch et al, Plenum Pub. Co., N.Y., N.Y. pp. 213 to 224) demonstrated that when patients with absorptive hypercalciuria are fed calcium gluconate, they exhibited increased urinary calcium, leading to an increased activity product ratio, a measure of the degree of urinary calcium oxalate saturation. Thus, calcium supplementation made them more prone to form kidney stones, since their urine became more supersaturated with respect to a common stone salt (calcium oxalate).

The interrelation of calcium and hypertension has been the focus of much recent research. McCarron et al (Science (1982) Vol. 217 pp. 267 to 269) found that subjects with essential hypertension had a lower daily calcium intake ($668\pm55$ mg) than that ($886\pm89$ mg) of normotensive subjects and hypertensive subjects had similar serum levels of total calcium, the hypertensive subjects had lower serum levels of ionized calcium. Ackley et al (Am. J. Clin. Nutr. (1983) Vol. 38 pp. 457 to 461) reported finding that hypertensive men consumed significantly less milk, a major source of dietary calcium, than did normotensive men.

Belizan et al (J. Am. Med. Ass'n. (1983 Vol. 249 No. 9 pp. 1161 to 1165) indicated that young adults showed reduction in blood pressure when their diets were supplemented with 1 gm/day elemental calcium (calcium carbonate or calcium lactate-gluconate). A similar observation was made with pregnant women (Belizan et al Am. J. Obstet. Gynecol (1983) Vol. 146 No. 2 pp. 175 to 180). Currently, a likelihood exists that adequate calcium intake may be an important factor in control of blood pressure.

Chronic diarrheal syndrome, where bone loss may occur, also sometimes involves calcium nephrolithiasis. This syndrome may result from surgical resection or inflammation of the digestive tract. Bone disease may occur because patients with this condition absorb calcium poorly from intestines. Kidney stones may develop from different causes including concentrated urine, undue acidity of urine and low urinary citrate. While these patients require calcium supplements for prevention of bone loss, they face the danger of forming more kidney stones when they take more calcium.

Supplementation of the diet with calcium appears to be an important step for control of adverse conditions such as, for example, osteoporosis, hypertension and bone loss in chronic diarrheal syndrome. Such calcium supplementation however, may cause undesirable effects, particularly nephrolithiasis.

Dietary calcium supplementation is generally agreed as most effective when the calcium is efficiently absorbed from the digestive tract. Thus a method of providing efficiently absorbed calcium while precluding calcium nephrolithiasis is needed.

An object of the present invention is to provide dietary calcium supplements which do not cause calcium nephrolithiasis. Another object of the present invention is to provide dietary calcium supplements which are efficiently absorbed. A further object of the present invention is to provide dietary calcium compositions with calcium citrate which may be readily compacted into easily ingested tablets with a satisfactorily high calcium content. Unless otherwise defined, the term "calcium citrate" is used herein as the tricalcium dicitrate species.

The present invention, as described subsequently herein, provides methods for accomplishing the above objectives and a product of superior qualities related to these objectives.

Prior attempts to form tabletized calcium citrate have led to tablets which were deemed inconveniently large when they contained, for example, as little as 150 milligrams of calcium. A further object of the present invention is the production of exceedingly dense calcium citrate tablets with an acceptable size and calcium content so that oral dietary calcium supplementation is more convenient and physically acceptable.

Other objects, advantages and features of the present invention will, upon examination of the accompanying descriptions and claims be apparent to those skilled in the pertinent arts.

SUMMARY OF THE INVENTION

A calcium citrate composition having a bulk density between 0.8 g/cc and 1.3 g/cc, preferably between 1.05 g/cc and 1.25 g/cc and most preferably between about 1.1 g/cc and 1.2 g/cc may be produced by methods of the present invention. Citric acid and a calcium compound selected from the group consisting of calcium carbonate, calcium oxide and calcium hydroxide are mixed to produce a mixture having a calcium compound/citric acid molar ratio of about 1.5. A hydrated mixture with a moisture content between about 30.5 weight percent and about 47.5 weight percent is produced by agitatively adding water to the mixture, although when desired the calcium compound, citric acid and water may be mixed in one step. The hydrated mixture is then blended to facilitate the reaction of citric acid with the calcium compound and to form a granulated mass primarily consisting of granules with diameters between about 1/64 inch and about 1/16 inch.

The granulated mass is then dried to a moisture content of between about 10 weight percent and about 13 weight percent to produce a calcium citrate composition having a bulk density greater than about 1.1 g/cc.

For the production of calcium citrate tablets this calcium citrate composition is a preferred precursor. A tableting calcium citrate composition is preferably formed by subjoining one or more of tableting binders such as cellulose gum, disintegrants such as sodium carboxymethylcellulose or lubricants such as magnesium stearate and into the calcium citrate composition and blending to form a tableting composition. There are many other pharmaceutically acceptable tableting binders, lubricants and disintegrants well-known in the pharmaceutical arts which are usable in the production of the tablets of the present invention. The tableting composition is then fed through a multiple-station tablet press to form calcium citrate tablets. The term citrate as used herein generally refers to the citrate radical as, for example, in the form of citrate tri-anion, citric acid or other citrate ions.

Calcium citrate tablets formed as described herein are generally greater than about 15 weight percent calcium and most usually have a calcium/citrate molar ratio of about 3/2. Such tablets preferably have a density greater than about 1.5 g/cc and may, for aesthetic or other purposes, be coated by conventional means with mixtures comprising substances such as sugar, polyvinylpyrrolidone, calcium carbonate and titanium dioxide, for example.

BRIEF DESCRIPTION OF THE PREFERRED EMBODIMENT

The present invention relates to the discovery that calcium citrate is a superior vehicle for dietary calcium supplementation. However, the ingestion of calcium citrate in a usual form presents potential problems. One potential problem, for example, is the bulkiness of usual calcium citrate which makes incorporating adequate amounts of calcium in a desired tablet size difficult. The present invention involves the discovery that exceedingly dense calcium citrate tablets may be made from bulk-form calcium citrate prepared in a particular fashion. The preferred fashion of bulk-form calcium citrate formulation comprises the reaction, in a dense hydrated mixture, of citric acid and a calcium compound selected from the group consisting of calcium carbonate, calcium oxide and calcium hydroxide. This dense hydrated mixture may be characterized as being a thick "slush" comprising calcium compound/citric acid combined in a molar ratio of about 3/2. The hydrated mixture has a preferable moisture content between about 30.5 weight percent and about 47.5 weight percent.

This hydrated mixture is blended, for example in a ribbon blender, until a granulated mass primarily consisting of granules with diameters between about 1/64 inch and about 1/16 inch is formed. The granulated mass is then dried to produce a calcium citrate composition having a moisture content between about 10 weight percent and about 13 weight percent, preferably about 12.6%. This calcium citrate composition has a bulk density (weight per gross volume) between about 0.80 g/cc and about 1.3 g/cc, preferably between 1.05 g/cc and 1.25 g/cc and more preferably between 1.1 g/cc and 1.2 g/cc. More extensive drying of the granulated mass with, for example, a fluid bed drier, may result in a calcium citrate composition unsuitable for the production of sufficiently dense calcium citrate tablets. Such an overly dried composition, having too little water and a bulk density less than about 0.80 g/cc, would be difficult to use for the production of dnse calcium citrate tablets by the processes of the present invention.

Bulk density was measured by: (1) placing a sample of the calcium citrate composition in a volumetrically graduated cylinder (for example, of 25 cc capacity); (2) tapping the cylinder for a period of time (usually about 1 minute) until the composition reached an apparently constant volume; (3) weighing the measured volume of composition; and (4) dividing the weight by the volume. Actual densities were measured for calcium citrate compositions prepared according to the processes of the present invention and for commercially obtained calcium citrate tetrahydrate. The density of the calcium citrate composition was about twenty percent higher than that of commercial calcium citrate when measured by helium-displacement and weighing methods.

X-ray crystallographic analyses of commercial calcium citrate tetrahydrate and of the calcium citrate composition of the present invention were performed and the results compared. These results indicated that the calcium citrate composition of the present invention comprised a form of calcium citrate tetrahydrate which was more compressible than commercial calcium citrate tetrahydrate.

Studies of surface area quantity and quality of calcium citrate composition of the present invention and of commercial calcium citrate tetrahydrate were performed. These surface area studies indicated that the commercial material was more porous and had much more surface area per unit of weight. The surface area per gram for the calcium citrate composition of the present invention was no more than about twenty percent of that found for commercial calcium citrate tetrahydrate. These surface area studies are also consistent with the more compressible nature of the calcium citrate composition of the present invention. The surface area range for the calcium citrate composition of the present invention is between about 0.7 m$^2$/g and about 2.0 m$^2$/g, preferably between about 0.7 m$^2$/g and about 0.8 m$^2$/g and most preferably between about 0.75 m$^2$/g and about 0.77 m$^2$/g. The upper surface area limit is less than about 2.0 m$^2$/g and the preferred surface area limit is 1.0 m$^2$/g. Scanning electron microscopy of the calcium citrate composition of the present invention and of commercial calcium citrate tetrahydrate revealed that the latter was much more porous than the former. This observation was again consistent with the greater compactibility of the calcium citrate composition of the present invention.

The following examples are provided to fully describe aspects of the present invention but are not intended to be limiting unless otherwise specifically so stated in the appended claims.

Such a calcium citrate composition may then be subjected to conventional tableting procedures to result in dense tablets having a density in excess of about 1.5 g/cc. In a preferred manner, the hydrated mixture is initially blended to form a solid white and granular appearing mixture. An alcohol possessing 2-3 carbon atoms such as ethanol, 1-propanol or 2-propanol is then subjoined to the granular appearing mixture to produce an alcoholized hydrated mixture comprising between about 3 weight percent and about 4 weight percent alcohol. The alcoholized hydrated mixture is then blended to form a granulated mass primarily consisting of granules with diameters between about 1/64 inch and about 1/16 inch. This granulated mass is finally dried to produce a calcium citrate composition having a density greater than about 1.1 gm/cc which may, in turn, be converted into dense tablets by conventional tableting procedures. Such tablets generally have a calcium content between about 16 weight percent and about 24 weight percent, preferably between 17 weight percent and 19 weight percent.

A tableting composition is preferably produced from the granulated mass obtained directly from the hydrated mixture, or from the alcoholized hydrated mixture, by subjoinment with a tableting binder such as cellulose gum (sodium carboxymethyl cellulose, Hercules Inc., Wilmington Del.), a lubricant such as magnesium stearate (Witco, Organics Division N.Y., N.Y. 10022) or disintegrants such as sodium carboxymethylcellulose. There are many other pharmaceutically acceptable tableting binders, lubricants and disintegrants well-known in the pharmaceutical arts which are usable in the production of the tablets of the present invention. Such tableting composition is then fed to a multi-station tablet press for compression into tablets. Tablets thus produced are termed "uncoated tablets" because of their as yet unapplied coating. The uncoated tablets preferably have a density between about 1.5 g/cc and about 2.4 g/cc, preferably between 1.7 g/cc and 2.2 g/cc and more preferably between 1.8 g/cc and 2.0 g/cc.

Tablet density was determined by an Archimedean method. A numbered and preweighed group of tablets (coated or uncoated) were immersed in a premeasured volume of a liquid not substantially dissolving calcium citrate such as an alcohol (e. g., ethanol or isopropanol), the liquid being contained in a volumetrically graduated cylinder. The increase in apparent alcohol volume was noted and taken as the tablet volume. The tablet density was the tablet weight divided by the tablet volume.

Uncoated tablets are preferably subjected to a final coating step with standard tablet coating agents such as, for example, polyvinylpyrrolidone (Wyandotte Corp., Parsippany, N.J. 07054), sugar, water, calcium carbonate and titanium dioxide. Coated tablets preferably have a density between about 1.3 g/cc and about 2.1 g/cc, more preferably between 1.5 g/cc and 2.0 g/cc and most preferably between 1.5 g/cc and 1.7 g/cc. These tablets constitute a pharmaceutically acceptable composition useful as a calcium supplement and each tablet contains at least about 150 mg calcium, preferably between about 150 mg and about 250 mg calcium and most preferably about 200 mg calcium.

The chemical reactions involved in calcium citrate production from calcium compounds and citric acid appear to be:

$$3CaCO_3 + 2C_6H_8O_7 \rightarrow Ca_3(C_6H_5O_7)_2 + 3CO_2 + 3H_2O \quad (1)$$

$$3CaO + 2C_6H_8O_7 \rightarrow Ca_3(C_6H_5O_7)_2 + 3H_2O \quad (2)$$

$$3Ca(OH)_2 + 2C_6H_8O_7 \rightarrow Ca_3(C_6H_5O_7)_2 + 6H_2O \quad (3)$$

While reaction (1) appears to be endothermic, requiring addition to the calcium carbonate and citric acid of water heated to a temperature between about 40° C. and about 80° C. Reactions 2 and 3 appear to be exothermic and proceed quite well with cold water, for example between about 0° C. and about 20° C. Those skilled in the art will recognize that citric acid may be reacted with appropriate mixtures of calcium carbonate, calcium hydroxide and calcium oxide.

It has been noted in the development of the present invention that, at least with the formation of calcium citrate from calcium carbonate, a two stage reaction appears to occur. Initially reaction (1) proceeds and then, as a possible second stage, the hydration of tricalcium dicitrate to form a tetrahydrate, which may be exothermic in character. These theories are again presented to most fully describe the present invention but are not meant to limit the invention should another theory prove more correct.

Among the discoveries described herein is the finding that citrate may play an unexpectedly important role in the enhancement of calcium solubility. For example it has been found that the solubility of calcium in a pH 3.0 aqueous solution increases when the calcium/citrate molar ratio decreases from about 3/2 to about 1/6. (see, e.g. Example 12).

Further investigations have established that calcium is more efficiently absorbed from the intestine to the blood as the calcium/citrate ratio of ingested calcium citrate dosages is decreased (e.g. when a calcium citrate preparation contains excess citric acid). Such a calcium citrate preparation may be used to produce tablets for immediate ingestion or may be dissolved in liquids or mixed with foods for ingestion. A precursor to such a calcium citrate preparation, a mixture of calcium carbonate and citric acid may be compacted into tablets which will, when immersed in water, effervesce and produce dissolved calcium citrate and citric acid suitable for ingestion.

In practice, preparations of calcium citrate useful in many practices of the present invention, where efficient absorption and solubility are sought, comprise calcium: (citrate-citric acid) molar ratios between about 1:1.2 and about 1:2. When tricalcium dicitrate is directly combined with citric acid to produce such ratios, these molar equivalencies may be viewed as combinations of tricalcium dicitrate and citric acid. For example, one mole of tricalcium dicitrate combined with four moles of citrate acid produces a calcium (citrate-citric acid) molar ratio and ½ and 1 tricalcium dicitrate plus 1.6 moles citric acid produces a calcium (citrate-citric acid molar ratio of 1/1.2. For simplicity herein a calcium/citrate molar ratio and a calcium/(citrate-citric acid) molar ratio are deemed as equivalent expressions.

The production of suitable calcium citrate tablets with a calcium/citrate molar ratio less than 3/2, while perhaps decreased in density as compared to those with a 3/2 ratio, should provide increased calcium bioavailability and thus be nutritionally satisfactory. The processes of tablet manufacture of the present invention should also provide optimally dense tablets with such calcium/citrate ratios. A tablet having a lower calcium/citrate-citric acid molar ratio and designed for oral administration may be prepared by the above-described tablet-making procedures to have a density and calcium content superior to that obtained by analogous conventional procedures.

It is contemplated that use of a tablet comprising calcium carbonate and citric acid in a molar ratio of from 1/1 to 1/6 should provide a convenient manner of producing a calcium supplementing beverage. Such a tablet would be effervescent when immersed in water and result in soluble and readily absorbable calcium citrate. Calcium oxide or calcium hydroxide may be substituted for calcium carbonate to produce a non-effervescent tablet which dissolves to produce a solution of calcium citrate-citric acid. These formulations, preferably in powdered or liquid form, may also be added to solid foods for supplementation thereof.

The following examples are provided to fully describe aspects of the present invention but are not intended to be limiting unless otherwise specifically so stated in the appended claims.

EXAMPLE 1

Tablet Production From Commercial Calcium Citrate

Calcium citrate (tricalcium dicitrate tetrahydrate) was obtained from Charles Pfizer Inc. (Chemical Division, N.Y., N.Y. 10017). Such calcium citrate had been conventionally produced by the precipitation with calcium ions of citric acid from an aqueous solution of citric acid and citrate. Pfizer calcium citrate (96 kg) was mixed thoroughly with 4 kg pregelatinized starch and 30 L $H_2O$. The resultant mixture was dried overnight at 150° F. and sized by passage through a Fitzmill No. 6 communator (Fitzpatrick) with a 3162AA screen. The sized material was blended with 1% magnesium stearate lubricant and 1% cellulose gum binder to form a tableting composition which had a bulk density less than 0.75 g/cc. This composition was tableted in a multiple station tablet press to form calcium citrate tablets. The uncoated calcium citrate tablets thus formed are described in Table 1.

TABLE 1

| Calcium Citrate Tablets From Commercial Calcium Citrate |
| --- |
| 0.8 cc/tablet |
| 1.185 g/cc |
| 1053 mg/tablet |
| 250 mg Ca/cc |
| 200 mg Ca/tablet |
| 19 wt % Ca |
| 3/2 Ca/citrate molar ratio |
| 831 mg $Ca_3$ (citrate)$_2$ |
| 10.1–10.3 mm width |
| 16.1 mm length |

EXAMPLE 2

Synthesis of Calcium Citrate By Conventional Methods

Calcium citrate was produced from citric acid and a calcium compound by several conventional methods. These conventional methods involved the precipitation of calcium citrate from an aqueous citric acid solution, particularly by the addition of calcium ions or a dilute slurry of a largely insoluble calcium compound such as calcium carbonate, oxide or hydroxide. The moisture content of such a conventional reaction mixture was over 50 weight percent. The calcium citrate compositions resulting from these syntheses all had bulk densities (measured volumetrically on a gross scale) of about 0.7 g/cc or less. These compositions were utilized to produce tablets similar to those described in Example 1.

These conventional methods of calcium citrate synthesis produced a composition unsuitable for production of the high density calcium citrate tablets of the present invention. It appears that when fine calcium citrate crystals form in an aqueous medium, a low density product only may be subsequently obtained.

EXAMPLE 3

Pilot Production of a Dense Calcium Citrate Composition

Calcium carbonate (150 g) and powdered citric acid (192 g) were mixed in a large beaker and 140 ml water (55° C.) was agitatively added thereto (i.e., with rapid stirring). After $CO_2$ evolution had slowed or ceased an apparent exothermic hydration of calcium citrate occurred to yield a dense (i.e. over 0.9 g/cc) granular hydrated calcium citrate. This dense granular calcium citrate was subjected to compression tableting and tablets containing 200 mg calcium with a size of 0.28 inch by 0.51 inch (about ½ the size of the tablets of Example 1) were produced, even without the addition of binding materials.

EXAMPLE 4

Large Scale Production of High Bulk Density Calcium Citrate and Tablets Thereof Calcium carbonate (136 kg, 1356 moles) and powdered citric acid (174 kg, 906 moles) were placed in a PK Gardner 28 cu. ft. ribbon mixer and blended for about 5 minutes. Hot water (120 L, 40° C.) was added rapidly at first and then at a reduced rate as frothing ensued until all 120 L was added.

Blending in the ribbon mixer was continued until the material began to appear solid, white and granular. At this point 2-propanol (16 L) was subjoined to the solid, white granular appearing mixture to assist in granulation. The blending was then continued until the granules of the granulated mass appeared to have diameters between about 1/64 inch and about 1/16 inch. Further blending would produce granules larger than 1/16 inch which are preferably avoided for ease of later drying, mixing and tableting.

The granulated mass was then removed from the blender and placed on drying trays in layers about ¾ inch thick. The granulated mass was then dried at a temperature of about 165° F. until the moisture content was between about 10% and about 13% to produce a dried calcium citrate composition with a bulk density greater than about 1.1 g/cc and usually less than about 1.25 g/cc.

Bulk density was measured by placing a weighed amount of calcium citrate composition in a volumetrically graduated 25 ml cylinder and tapping the cylinder until a constant volume was reached. The weight per unit volume was then calculated. True densities of calcium citrate preparations were measured by the displacement of helium gas by preweighed amounts, using a Micrometrics Model 1320 AutoPyncnometer. A density value between about 2.4 g/cc and about 2.5 g/cc was obtained for the calcium citrate composition of the present invention. A preferred density range is between about 2.2 g/cc and about 2.6 g/cc. A corresponding density value of about 2.0 g/cc was obtained for Pfizer calcium citrate tetrahydrate.

Surface area measurments of the calcium citrate composition of the present invention and commercial calcium citrate tetrahydrate were conducted. The standard B.E.T. procedure of Brunauer et alia (J. Am. Chem. Soc. 59, 2682 (1937) and J. Am. Chem. Soc. 60, 309 (1938)) was used for these surface area measursments. The commercial calcium citrate tetrahydrate had a surface area of about 10 m$^2$/g and the calcium citrate composition of the present invention had a surface area of about 1/10 this value.

The dried calcium citrate composition was subjoined with 1.5 weight percent magnesium stearate and 1 weight percent cellulose gum and passed through a Fitzmill model no. 6 communator (Fitzpatrick) with a 3162AA screen and blended for about 5 minutes to form a tableting composition. The screen size preferred is one which permits the production of particles large enough to flow yet small enough to prevent packing.

The tableting composition was then tableted in a multiple station tablet press to form calcium citrate tablets comprising at least about 150 mg calcium. Multiple station tablet presses such as a Cotton #216-16 station press; a Vector #247-41 station press; or a Manesty rotopress-37 station press, for example may be used.

The tablets thus obtained may be final products or may be further processed.

Further processing to physically and aesthetically improve these tablets may be accomplished by tablet coating procedures well-known to those skilled in relevant pharmaceutical arts. For example, a coating comprising polyvinylpyrrolidone (PVP), sugar, water, calcium-carbonate and titanium dioxide was placed on tablets comprising 200 mg calcium. This coating procedure was by conventional pharmaceutical pan-coating technology.

EXAMPLE 5

Variation in High Bulk Density Calcium Citrate Composition Production Using Calcium Carbonate Calcium carbonate (300 moles) was thoroughly mixed with 200 moles citric acid (anhydrous or hydrated citric acid are both usable). This mixing may be accomplished in well-known variety of manners. It has been found that a quantity of heated water (50° C.–80° C.) between 30 kg and 60 kg, preferably between about 40 kg and about 50 kg should be gradually added (more rapidly of first) with continuous mixing until the mass of material attains a granular consistency. This material may then be dried, for example at a temperature between about 60° C. and about 80° C., until the moisture content is between about 10 weight percent and about 13 weight percent. These variations are meant to summarize the results of many months of experimentation in this area and to elucidate workable variations in the preferred embodiment presented in Example 4.

EXAMPLE 6

High Bulk Density Calcium Citrate From Calcium Oxide

The procedure of Example 5 was followed with the calcium carbonate being replaced by calcium oxide. The water was added at a uniform rate and its temperature was cold (0° C. to 20° C.). A calcium citrate composition having a bulk density slightly greater than 1.1 g/cc was produced.

EXAMPLE 7

Use of Calcium Hydroxide

The procedure of Example 6 was followed but with calcium hydroxide in place of calcium oxide. A calcium citrate composition having a bulk density greater than 1.1 g/cc was again produced.

EXAMPLE 8

Use of Aqueous Citric Acid

The procedures of Examples 5, 6 or 7 were followed but with 200 moles of citric acid being added as a 50% aqueous citric acid solution and the separate water addition being deleted. Again calcium citrate compositions having bulk densities greater than 1.1 g/cc were produced.

EXAMPLE 9

Calcium Citrate Compositions With Excess Citric Acid

The procedures of Example 5 were followed but the amount of citric acid was increased 120% to 300%. The resultant calcium citrate-citric acid composition was dried to a moisture content of less than about 2 weight percent and found to be suitable for tableting.

Calcium citrat (1 mole) and citric acid (1 mole) were blended and then mixed with water (10 mole at 60° C.). After thorough blending the mixture was dried at 170° F. for 2 days. The dried composition had a bulk density of about 0.85 g/cc. The dried composition was mixed with 4 weight percent microcrystalline cellulose (FMC Corp., Newark, Del. 19711), 1 weight percent magnesium stearate and 1 weight percent cellulose gum to produce a tableting composition.

The tableting composition was then processed through a conventional multistation tableting press to produce tablets having a calcium/(citrate-citric acid) molar ratio of 1/1. Properties of these 1/1 calcium citrate tablets are shown in Table 2.

TABLE 2

| Calcium/Citrate 1/1 Tablets |
|---|
| 0.71 cc/tablet |
| 1.39 g/cc |
| 990 mg/tablet |
| 211 mg Ca/cc |
| 150 mg Ca/tablet |
| 15.2 wt % Ca |
| 1/1 Cacitrate/citric acid molar ratio |
| 16.1 mm length |
| 10.5 mm width |

EXAMPLE 10

Characterization of Calcium Citrate Tablets

Both uncoated tablets and coated tablets (Citracal TM) produced by the processes of Example 4 were examined for weight, volume, calcium content and size. The data in Table 3 describe the direct and indirect results of these measurements. As may be seen in Table 3, a tablet comprising at least about 820 mg tricalcium dicitrate may be produced having a volume less than about 0.7 cc.

TABLE 3

| | Calcium Citrate Tablets | |
|---|---|---|
| | Uncoated | Coated |
| cc/tablet | 0.53 | 0.66 |
| g/cc | 1.89 | 1.63–1.742 |
| mg/tablet | 1008 | 1075–1150 |
| mg Ca/cc | 375. | 303 |
| mg Ca/tablet | 199 | 200 |
| wt % Ca | 19.84 | 18.6–17.39 |
| Ca/citrate molar ratio | 1.5 | 1.5 |
| mg $Ca_3(citrate)_2$ | 830 | 831 |
| width (mm) | 10.1–10.2 | 10.35–10.5 |
| length (mm) | 12.8 | 13.4 |

EXAMPLE 11

Preparation of Calcium Citrate-Citric Acid

Calcium citrate with excess citric acid was prepared as follows. Specific amounts of calcium carbonate and citric acid at a molar ratio of 3:2 (i.e., 1.5) were thoroughly mixed. Warm water (50° C.–80° C.) was gradually added with agitation to form a hydrated mixture containing about 40 weight percent water. Agitation was continued until $CO_2$ evolution had apparently ceased. Additional amounts of citric acid were then added and thoroughly mixed to produce the calcium/citrate molar ratios shown in Table 4 (Example 12). The tricalcium dicitrate and tricalcium dicitrate-citric acid compositions were then dried at 60° C. to 80° C. to a moisture content of less than about 5 weight percent.

EXAMPLE 12

Solubility of Calcium Citrate As A Function of Excess Citrate

An excess (more than will dissolve) of each of the various calcium citrate and calcium citrate-citric acid preparations described in Example 11 and Table 4 was added to water maintained at a temperature of 37° C. and at pH 3.0 by titration with HCl or NaOH every 15 minutes. To establish equilibration each mixture was stirred for 2 hours. After filtration of solids, the calcium content of each filtrate was measured by atomic absorption spectrophotometry. The pH of 3.0 was chosen as approximating the upper pH of basal gastric fluid. As shown in Table 4, excess citric acid increased the solubility of calcium 6-fold to 15-fold.

TABLE 4

| | Calcium Citrate Solubility | | | |
|---|---|---|---|---|
| Sample | Mole Ca/ Mole Citrate | Ratio | Mg Ca/ Liter Filtrate | Relative Ca Solubility |
| Control | 1/0.67 | 1.5 | 610 | 1 |
| 1 | 1/0.80 | 1.25 | 4180 | 6.85 |
| 2 | 1/0.90 | 1.11 | 4410 | 7.23 |
| 3 | 1/1.0 | 1.0 | 3980 | 6.52 |
| 4 | 1/1.25 | 0.8 | 3740 | 6.13 |
| 5 | 1/1.5 | 0.67 | 5400 | 8.85 |
| 6 | 1/2 | 0.5 | 6820 | 11.18 |
| 7 | 1/3 | 0.33 | 9630 | 15.78 |
| 8 | 1/6 | 0.17 | 9640 | 15.15 |

EXAMPLE 13

Intestinal Calcium Absorption From Calcium Citrate vs Calcium Citrate-Citric Acid Three subjects were orally administered 0.5 g calcium as solid control calcium citrate (3/2 ratio) in one study and as calcium citrate-citric acid (Table 4, sample no. 5, 0.67 ratio) in a second study. Urine in the second 2 hr period following the administration was collected and assayed for dissolved calcium by atomic absorption spectrophotometry. The increment in urinary calcium during the second 2 hr period after the calcium administration provided an indirect measure of calcium absorption. The calcium was better absorbed from calcium citrate enriched with citric acid than from control calcium citrate (Table 5).

TABLE 5

| Urinary Calcium Concentration Calcium Dosage Form | | |
|---|---|---|
| (Control) Ca/cit = 3/2 | | (5) Ca/cit = 2/3 |
| | Increment in Urinary Calcium | |
| Subject | mg/dl GF* | mg/dl GF |
| 1 | 0.061 | 0.140 |
| 2 | 0.187 | 0.241 |
| 3 | 0.036 | 0.047 |

*mg per deciliter glomerular filtrate

As in evident from Table 5, urinary calcium is elevated when an excess of citric acid is administered with tricalcium dicitrate. This observation is consistent with an increased efficiency of calcium absorption when excess citric acid is present and may lead to a new understanding of dietary calcium requirements.

EXAMPLE 14

"Effervescent" Preparations Suitable for Adding Calcium Citrate to Liquids

Solid preparations of basic or modified calcium citrates may not be suitable for enriching soft drinks or liquids with calcium, because they sometimes dissolve too slowly or incompletely. One rapid or complete way of dissolving calcium citrate involves the use of "effervescent" preparations. Such effervescent preparations may be made and used as follows:

Solid preparations of calcium carbonate and citric acid in exactly desired ratio are mixed. When this mixture is added to water, the reaction of the two compounds yields calcium citrate, with elaboration of carbon dioxide. An excess of citrate renders calcium citrate increasingly soluble.

Four different effervescent calcium citrate preparations were prepared. Each contained 400 mg of elemental calcium (10 mmoles) as calcium carbonate. In addition, sample 1 had 15 mmoles of citric acid, sample 2 had 12.5 mmoles of citric acid, sample 3 had 10 mmoles of citric acid, and sample 4 had 6.7 mmoles of citric acid. Thus, calcium:citrate molar rations were 1:1.5, 1:1.25, 1:1 and 1:0.67 (tricalcium dicitrate) for samples 1 to 4, respectively.

Each effervescent calcium citrate preparation was suspended in 300 ml of distilled water kept at 37° C. Samples 1 and 2 completely dissolved in 5 minutes but samples 3 and 4 with lower Ca:citrate ratios did not completely dissolve in 1 hour. At the end of one hour, greater than 98% of calcium and citrate could be kept in solution in samples 1 and 2 (with Ca:citrate molar ratios of 1:1.5 and 1:1.25), indicating complete dissolution. However, in sample 3 (with Ca:citrate ratio of 1:1) only 73% of calcium and 84% of citrate could be kept in solution, and in sample 4 (with Ca:citrate of 1:0.67) only 56% of calcium and 63% of citrate were soluble.

Thus, a liquid preparation containing 400 mg of calcium as calcium citrate/300 ml could be prepared from solutions 1 and 2 with surplus of citrate, but not from solutions 3 and 4 with a slight or without citrate surplus. An excess of citrate therefore imparts increased solubility of calcium citrate even when it is prepared from calcium carbonate and citric acid. Analogous non-effervescent preparations with similar solubility properties may be prepared with calcium oxide or calcium hydroxide substituted for calcium carbonate.

Effervescent tablets or non-effervescent but soluble tablets may be prepared by admixture of a calcium compound such as calcium carbonate, calcium oxide or calcium hydroxide with citric acid in a molar ratio of calcium compound: citric acid between about 1:2 and about 1:1.2.

EXAMPLE 15

Use of Calcium Citrate in High Calcium Soft Drink Mix

A mixture of calcium hydroxide or calcium oxide with powdered citric acid was prepared so that when the mixture is added to an aqueous media with or without flavor or carbonation a solution of soluble calcium citrate is formed within the object solution. This solution, comprising a finished soft drink, contained calcium citrate formed in the reaction of calcium hydroxide (or oxide or carbonate) and citric acid. The calcium citrate present provides calcium in an easily absorbed form which is tasteless and which has enhanced physiological uptake when contrasted to other calcium supplements. It is established that this form of calcium supplementation also has reduced risk for kidney stone formation.

A mixture of 1 mole of calcium hydroxide and a range from 0.67 to 1.5 moles citric acid each in dry powder were blended to make a uniform fine particle mixture. When 728.9 mg. of this mixture was added to 333 ml of cold water virtually instant solubilization occurred and provided a tasteless solution containing 100 mg. elemental calcium as the citrate. This calcium presentation has enhanced bioavailability and decreased risk for nephrolithiasis.

This mixture may be scaled upward or downward in quantity to provide a mixture suitable for calcium enhancement of an established drink or drink base. At a level of 400 mg. elemental calcium in 355 ml of drink volume a faintly perceptable citric acid taste is noted. In most drink flavors this presence tends to enhance existing flavors and to a lesser extent, sweetness seems to be enhanced as well, particularly if artificial sweeteners such as aspartame, saccharine or cyclamate are used.

EXAMPLE 16

X-ray Analysis of Calcium Citrate

X-ray powder diffraction analyses of calcium citrate composition samples of the present invention and of commercial calcium citrate tetrahydrate samples (Pfizer) were performed through the aid of Dr. Neil S. Mandel, Professor of Medicine, Biochemistry and Orthopedic Surgery and Director, National VA Crystal Identification Center; Veterans Administration Medical Center, 5000 West National Avenue, Research Service/151, Wood, Wis. 53193.

The calcium citrate samples were ground in an agate mortar and pestle and put through a 37um sieve. They were then irradiated with $Cu-K_{alpha\ 1}$ radiation on a Rigaku high brilliance rotating anode x-ray generator. A germanium crystal monochromated Huber high resolution Guinier powder diffraction camera was used to monitor x-ray diffraction patterns. The samples were irradiated for 2.5 hours at room temperature under constant rotation to avoid preferred orientation. The direct beam was imaged on the film and used as the internal standardization of absolute 0.00.

The results of these analyses were: Commercial calcium citrate tetrahydrate (P) showed a diffraction pattern indicating that it was approximately 90-95% pure calcium citrate tetrahydrate. This analysis was conducted by comparing diffraction data with those of standard #25-1568 from the organic file of the Joint Commission on Powder Diffraction Standards (Philadelphia, Pa.). There were 14 diffraction maxima measured to d=2.83 Angstrom, with 1 diffraction maxima at 5.037 Angstrom not being accounted for by the calcium citrate standard pattern. Although the d-spacings for sample P were very similar to that described in the citrate standard, some of the diffraction intensities did not agree. For example, the first observed diffraction line at 15.357 Angstrom had a measured intensity of strong and the corresponding line in the standard has an intensity of 100. The second line at 7.648 Angstrom had a measured intensity of medium strong which corresponded with a tabulated standard intensity of 50. However, the seventh line at 3.903 Angstrom which had a measured intensity of strong, had only a tabulated standard intensity, even assuming that the 2 lines at 3.94 and 3.89 Angstrom were merged together to 1 line. Similarly, line #9 at 3.500 Angstrom had a measured intensity of medium, corresponding to an intensity of 2.

The calcium citrate composition of the present invention (MD) showed 13 diffraction maxima recorded to 2.57 Angstrom, with one line at 16.754 Angstrom not being accounted for by the calcium citrate standard. The intensities for some lines (e.g. lines 2, 5, & 7) were in error when compared to the standard (as also shown with sample P). The diffraction lines for sample MD were notably and consistently broader than the diffraction lines for sample P.

These x-ray diffraction patterns were consistent with the ability of the calcium citrate composition of the present invention (sample MD) being more compressible than commercial calcium citrate tetrahydrate (sample P). As a general rule, the narrowness of diffraction lines correlates with the largeness of the domain size and the better the degree of crystalinity in a sample. Conversely, the broader diffraction lines of the calcium citrate composition of the present invention indicated that it had a poorer degree of crystalinity, a smaller domain size and was therefore likely to be more easily compactible.

Changes may be made in the construction, operation and arrangement of the various components, steps and procedures described herein without departing from the concept and scope of the invention as defined in the following claims.

What is claimed is:

1. A method for producing a calcium citrate composition having a bulk density greater than about 1.1 g/cc, the method comprising:
   mixing citric acid and a calcium compound selected from the group consisting of calcium carbonate, calcium oxide and calcium hydroxide, to produce a mixture having a calcium compound/citric acid molar ratio of about 3/2;
   adding water agitatively to the mixture to form a hydrated mixture with a moisture content between about 30.5 weight percent and about 47.5 weight percent;
   blending the hydrated mixture to form a granulated mass primarily consisting of granules with diameters between about 1/64 inch and about 1/16 inch; and
   drying the granulated mass to a moisture content of between about 10 weight percent and about 13 weight percent to produce a calcium citrate composition having a bulk density greater than about 1.1 g/cc.

2. The method of claim 1 wherein, directly after the adding step, the steps are added of:
   initially blending the hydrated mixture to form a solid, white and granular-appearing mixture;
   subjoining an alcohol selected from the group consisting of ethanol, 1-propanol and 2-propanol to the solid, white and granular-appearing mixture to produce an alcoholized hydrated mixture comprising between about 3 weight percent and about 4 weight percent alcohol;
   and the blending step is defined further as:
   blending the alcoholized hydrated mixture to form a granulated mass primarily consisting of granules with diameters between about 1/64 inch and about 1/16 inch.

3. The method of claim 1 or claim 2 wherein the calcium compound is calcium carbonate.

4. The method of claim 3 wherein the water has a temperature between about 40° C. and about 80° C.

5. The method of claim 4 wherein the adding step is defined further as:
   adding water agitatively and rapidly at first until frothing occurs and then at a reduced rate to form a hydrated mixture with a moisture content between about 37 weight percent and about 42 weight percent.

6. The method of claim 1 or 2 wherein the calcium compound is calcium oxide or calcium hydroxide and the water is at a temperature between about 0° C. and about 20° C.

7. The method of claim 1 or 2 wherein the calcium compound consists essentially of calcium carbonate, calcium hydroxide, calcium oxide or a mixture thereof.

8. The method of claim 2 wherein the alcoholized hydrated mixture comprises about 3.6 weight percent alcohol.

9. A tablet consisting essentially of calcium citrate, containing at least about 150 mg. calcium, having a density greater than about 1.5 g/cc and with a calcium/citrate molar ratio of about 1.5.

10. A tablet consisting essentially of calcium citrate, being greater than about 15 weight percent calcium, having a calcium/citrate molar ratio of about 3/2, and having a density greater than 1.3 g/cc.

11. A tablet consisting essentialy of at least about 820 mg. tricalcium dicitrate and a volume less than about 0.7 cc.

12. The tablet of claim 9, 10 or 11 defined further as comprising magnesium stearate and cellulose gum.

13. The tablet of claim 12 defined yet further as comprising about 1.5 weight percent magnesium stearate and about 1 weight percent cellulose gum.

14. The tablet of claim 12 defined further as having a coating comprising: polyvinylpyrrolidone, sugar, calcium carbonate and titanium dioxide.

15. A process for producing calcium citrate tablets comprising at least about 150 mg. calcium, having a density greater than about 1.5 g/cc and a calcium/citrate molar ratio of about 3/2, the process comprising:
   mixing citric acid and a calcium compound selected from the group consisting of calcium carbonate, calcium hydroxide and calcium oxide to produce a mixture, the calcium compound/citric acid molar ratio being about 3/2;
   adding water agitatively to the mixture to form a hydrated mixture with a moisture content between about 30.5 weight percent and about 47.5 weight percent;
   blending the hydrated mixture to facilitate reaction of the citric acid with the calcium compound and the formation of a granulated mass, the blending being halted when the granulated mass primarily consists of granules with diameters between about 1/64 inch and about 1/16 inch;
   drying the granulated mass to a moisture content between about 10 weight percent and about 13 weight percent to produce a dried calcium citrate composition having a bulk density greater than about 1.1 g/cc;
   subjoining one or more tableting binders such as magnesium stearate and cellulose gum into the calcium citrate composition and blending the subjoinment to form a tableting composition; and
   tableting said tableting composition in a multiple station tablet press to form calcium citrate tablets comprising at least about 150 mg. calcium, having a density greater than about 1.5 g/cc and a calcium/citrate molar ratio of about 3/2.

16. The process of claim 15 defined further as including a final coating step wherein the calcium citrate tablets are coated with a mixture comprising polyvinylpyrrolidone, sugar, water, calcium carbonate and titanium dioxide.

17. A tablet consisting essentially of calcium citrate and citric acid in a calcium/(citrate-citric acid) molar ratio of about 1/1, said tablet being about 15.2 weight percent calcium and having a density of at least about 1.39 g/cc.

18. A tablet consisting essentially of calcium citrate, containing 16–24% by weight calcium, having a density of 1.5–2.4 g/cc and having a volume less than 0.7 cc.

19. A tablet consisting essentially of calcium citrate and having a density greater than about 1.1 g/cc.

20. A tablet of claim 19 wherein the calcium citrate is tricalcium dicitrate.

21. A composition of matter consisting essentially of calcium citrate having a density between about 2.2 g/cc and about 2.6 g/cc.

22. The composition of matter of claim 21 wherein the density is between 2.4 g/cc and 2.5 g/cc.

23. A calcium citrate tablet comprising 16–24% calcium, having a density greater than about 1.5 g/cc and with a calcium/citrate molar ratio of about 1.5.

24. A composition of matter consisting essentially of high bulk density calcium citrate in which the ratio of calcium ion to citrate ion is about 3 to 2 and the bulk density is between about 0.8 g/cc and about 1.3 g/cc.

25. The composition of matter of claim 24 wherein the bulk density is between 1.05 g/cc and b 1.25 g/cc.

26. The composition of matter of claim 24 wherein the bulk density is between 1.1 g/cc and 1.2 g/cc.

27. The composition of matter of claim 24 or 21 wherein high bulk density calcium citrate has 13 x-ray diffraction maxima recorded to 2.57 Angstrom when powdered and subjected to Cu-K$_{alpha\ 1}$ radiation.

28. The composition of matter of claim 24 or 21 wherein the high bulk density calcium citrate is defined further as having a surface area and the surface area is less than about 2.0 m$^2$/g.

29. The composition of matter of claim 28 wherein the surface area is less than about 1.0 m$^2$/g.

30. The composition of matter of claim 28 wherein the surface area is composition of matter of claim 28 wherein the surface area is between about 0.7 m$^2$/g and about 1.0 m$^2$/g.

31. The composition of matter of claim 28 wherein the surface area is between about 0.7 m$^2$/g and about 0.8 m$^2$/g.

32. The composition of matter of claim 28 wherein the surface area is between about 0.75 m$^2$/g and about 0.77 m$^2$/g.

33. A composition of matter consisting essentially of calcium citrate having a density between about 2.4 g/cc and about 2.5 gg/cc.

34. A pharmaceutical composition useful as a calcium supplement comprising a composition of matter according to claim 24 or 21 in an amount effective for calcium supplementation and a pharmaceutically acceptable carrier therefor.

35. A pharmaceutical composition according to claim 34 which is useful as calcium supplement in the treatment of osteoporosis.

36. A pharmaceutical composition according to claim 34 comprising an amount of calcium citrate equivalent to 150 mg to 250 mg of calcium.

37. A pharmaceutical composition according to claim 34 comprising an amount of calcium citrate equivalent to about 200 mg of calcium.

38. A pharmaceutical composition according to claim 34 comprising an amount of calcium citrate equivalent to a minimum of b 150 mg of calcium.

39. A pharmaceutical composition according to claim 34 useful as a calcium supplement, the composition comprising calcium citrate in a amount effective for calcium supplementation and citric acid in a mole ratio of calcium citrate to citric acid of from about 1:4 to 1:1.6 and a pharmaceutically acceptable carrier therefor.

40. A pharmaceutical composition according to claim 34 in which the mole ration of calcium citrate to citric acid is 1:1.

41. A method of supplementing dietary calcium which comprises administering the composition of matter according to claim 24 to a subject in need of said supplement in an amount effective for calcium supplementation.

42. A method according to claim 41 wherein the subject has osteoporosis and the composition of matter is administered in an amount effective for the treatment of the osteoporosis.

43. A method according to claim 41 in which 0.25 to 2.0 grams of calcium are administered daily.

44. A method according to claim 41 in which 0.5 to 1.0 grams of calcium are administered daily.

* * * * *

UNITED STATES PATENT AND TRADEMARK OFFICE
CERTIFICATE OF CORRECTION

PATENT NO. : 4,814,177

DATED : March 21, 1989

INVENTOR(S) : Walsdorf et al

It is certified that error appears in the above-identified patent and that said Letters Patent is hereby corrected as shown below:

In Claim 30, Column 17, lines 50-51 delete the words "wherein the surface area is composition of matter of claim 28"

In Claim 33, Column 18, Line 11, delete "gg/cc" and insert --g/cc--.

In Claim 35, Column 18, Line 18, insert the word "a" between the words "as" and "calcium".

In Claim 39, Column 18, Line 31 delete the word "a" between the words "in" and "amount" and insert the word --an--.

Signed and Sealed this

Seventeenth Day of September, 1991

Attest:

HARRY F. MANBECK, JR.

Attesting Officer

Commissioner of Patents and Trademarks